US007593626B2

(12) United States Patent
Kato (10) Patent No.: US 7,593,626 B2
(45) Date of Patent: Sep. 22, 2009

(54) OPTICAL TOMOGRAPHY SYSTEM

(75) Inventor: Kiichi Kato, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 307 days.

(21) Appl. No.: 11/529,437

(22) Filed: Sep. 29, 2006

(65) Prior Publication Data

US 2007/0077045 A1 Apr. 5, 2007

(30) Foreign Application Priority Data

Sep. 30, 2005 (JP) ............................. 2005/289117

(51) Int. Cl.
*A61B 1/04* (2006.01)
*G01B 9/02* (2006.01)

(52) U.S. Cl. .......................................... 396/17; 356/479
(58) Field of Classification Search ................... 396/17; 356/479, 497
See application file for complete search history.

(56) References Cited

U.S. PATENT DOCUMENTS

| | | | |
|---|---|---|---|
| 5,202,745 A * | 4/1993 | Sorin et al. ................ 356/73.1 |
| 5,291,267 A * | 3/1994 | Sorin et al. ................. 356/479 |
| 5,321,501 A * | 6/1994 | Swanson et al. ............ 356/479 |
| 5,365,335 A * | 11/1994 | Sorin ......................... 356/479 |
| 5,459,570 A * | 10/1995 | Swanson et al. ............ 356/479 |
| 6,069,698 A * | 5/2000 | Ozawa et al. ............... 356/511 |
| 6,134,003 A * | 10/2000 | Tearney et al. ............. 356/479 |
| 6,421,164 B2 * | 7/2002 | Tearney et al. ............. 359/287 |
| 6,485,413 B1 * | 11/2002 | Boppart et al. ............. 600/160 |
| 6,501,551 B1 * | 12/2002 | Tearney et al. ............. 356/477 |
| 6,564,089 B2 * | 5/2003 | Izatt et al. ................... 600/478 |
| 6,615,072 B1 * | 9/2003 | Izatt et al. ................... 600/478 |
| 6,628,401 B2 * | 9/2003 | Toida ......................... 356/479 |
| 6,636,755 B2 * | 10/2003 | Toida ......................... 600/407 |
| 6,735,463 B2 * | 5/2004 | Izatt et al. ................... 600/476 |
| 7,072,046 B2 * | 7/2006 | Xie et al. .................... 356/479 |
| 7,187,450 B2 * | 3/2007 | Drabarek .................... 356/497 |
| 7,324,211 B2 * | 1/2008 | Tsujita ........................ 356/497 |
| 7,408,648 B2 * | 8/2008 | Kleen et al. ................. 356/479 |
| 2003/0103212 A1 * | 6/2003 | Westphal et al. ............ 356/479 |
| 2004/0181148 A1 * | 9/2004 | Uchiyama et al. .......... 600/425 |
| 2006/0170930 A1 * | 8/2006 | Li ............................... 356/479 |
| 2007/0076213 A1 * | 4/2007 | Kato ........................... 356/479 |

FOREIGN PATENT DOCUMENTS

JP 2003-172690 A 6/2003

* cited by examiner

*Primary Examiner*—Rodney E Fuller
(74) *Attorney, Agent, or Firm*—Sughrue Mion, PLLC (57) ABSTRACT

Light emitted from the light source unit divided into measuring light and reference light. An optical path length of the measuring light or the reference light is adjusted and a probe guides the measuring light to an object. The reflected light from the object when the measuring light is projected onto the object and the reference light are multiplexed. Interference light of the reflected light and the reference light which have been multiplexed is detected, and a tomographic image of the object is obtained on the basis of the interference light. The probe is provided with a distance measuring circuit for measuring the distance from the probe to the object, and the optical path length of the measuring light or the reference light is adjusted by the use of the distance to the object measured by the distance measuring circuit to adjust the tomographic image obtainment initiating position.

9 Claims, 5 Drawing Sheets

OPTICAL TOMOGRAPHY SYSTEM

BACKGROUND OF THE INVENTION

1. Field of the Invention

This invention relates to an optical tomography system for obtaining an optical tomographic image by measurement of OCT (optical coherence tomography).

2. Description of the Related Art

As a system for obtaining a tomographic image of an object of measurement in a body cavity, there has been known an ultrasonic tomography system. In addition to such an ultrasonic tomography system, there has been proposed an optical tomography system where an optical tomographic image is obtained on the basis of an interference of light by low coherence light. See, for instance, Japanese Unexamined Patent Publication No. 2003-172690. In the system disclosed in Japanese Unexamined Patent Publication No. 2003-172690, an optical tomographic image is obtained by measuring TD-OCT (time domain OCT) and the measuring light is guided into the body cavity by inserting a probe into the body cavity from the forceps port of an endoscope by way of a forceps channel.

More specifically, low coherence light emitted from a light source is divided into measuring light and reference light and the measuring light is projected onto the object of measurement, while the reflected light from the object of measurement is led to a multiplexing means. The reference light is led to the multiplexing means after its optical path length is changed. By the multiplexing means, the reflected light and the reference light are superposed one on another, and interference light due to the superposition is detected by, for instance, heterodyne detection. In the TD-OCT measurement, a phenomenon that interference light is detected when the optical path of the measuring light conforms to the optical path of the reference light in length is used and the measuring position (the depth of measurement) in the object is changed by changing the optical path length of the reference light.

When measuring the OCT by inserting a probe into a body cavity, the probe is mounted on the system body to be demountable since disinfection, cleaning and the like of the probe after use are necessary. That is, a plurality of probes are prepared for one optical tomography system and the probes are changed by the measurement. However there is an individual difference in the length of the optical fiber due to the manufacturing errors and the like, and the optical path length of the measuring light can change each time the probe is changed. Accordingly, in Japanese Unexamined Patent Publication No. 2003-172690, on the basis of the reflected light from the inner surface of a tube (sheath) covering an optical fiber of the probe, the optical path length of the reference light is adjusted to conform to the optical path length of the measuring light.

Whereas, as a system for rapidly obtaining a tomographic image without changing the optical path length of the reference light, there has been proposed an SS-OCT (swept source OCT) system where interference light is detected while the frequency of the light emitted from the light source is changed with time. In the SS-OCT system, an interferogram interference intensity signal is obtained without changing the optical path length by sweeping the frequency of the laser beam emitted from the light source to cause the reflected light and the reference light to interfere with each other by the use of a Michelson interferometer. Then a tomographic image is generated by carrying out a Fourier analysis on the interferogram signal in the region of an optical frequency.

Whereas, as a system for rapidly obtaining a tomographic image without sweeping the optical path length of the reference light, there has been proposed an optical tomography method of obtaining an optical tomographic image by measurement of SD-OCT (spectral domain OCT). In the SD-OCT system, a tomographic image is formed without scanning in the direction of depth, by emitting broad band, low coherence light from a light source by the use of a Michelson interferometer, dividing the low coherence light into measuring light and reference light and carrying out a Fourier analysis on each channeled spectrum obtained by decomposing the interference light of the reflected light, which returns when projecting the measuring light onto the object, and the reference light into frequency components.

SUMMARY OF THE INVENTION

Though, in Japanese Unexamined Patent Publication No. 2003-172690, the optical path length is adjusted in order to deal with the individual difference in probes, it is necessary to adjust the measurement initiating position for positioning the object in a range obtainable by the OCT measurement. That is, the measurable range in the direction of depth measurable (tomographic image obtainable) by the OCT measurement is limited, and the optical path length of the reference light must be adjusted according to the distance between the probe and the object so that the measurement initiating position is adjusted to position the object in the measurable range.

Since the TD-OCT measurement is for adjusting the optical path length of the reference light to change the depth to be measured, the measurable range can be adjusted by adjusting the optical path length while observing, for instance, the signal intensity and/or the signal shape by the beat signal measurement and/or the interferogram measurement of the interference light. However, since reflection information in the positions of depth cannot be obtained unless a frequency analysis processing such as Fourier-transform on the interference light in the SS-OCT measurement and the SD-OCT measurement, a frequency analysis processing is necessary when the position of the object is checked to adjust the measurement initiating position, which takes a long time to adjust the measurement initiating position.

In view of the foregoing observations and description, the primary object of the present invention is to provide an optical tomography system which can adjust the measurement initiating position in a short time.

In accordance with the present invention, there is provided an optical tomography system for obtaining a tomographic image of an object to be measured comprising a light source unit which emits light, a light dividing means which divides light emitted from the light source unit into measuring light and reference light, an optical path length adjusting means which adjusts an optical path length of the measuring light or the reference light which has been divided by the light dividing means, a probe which guides the measuring light to the object, a multiplexing means which multiplexes the reflected light from the object when the measuring light is projected onto the object and the reference light, an interference light detecting means which detects interference light of the reflected light and the reference light which have been multiplexed by the multiplexing means, and a tomographic image obtaining means which obtains a tomographic image of the object on the basis of the interference light detected by the interference light detecting means, wherein the improvement comprises that the probe is provided with a distance measuring means for measuring the distance from the probe to the object, and the optical path length adjusting means adjusts the optical path length of the measuring light or the reference light by the use of the distance to the object measured by the distance measuring means to adjust the tomographic image obtainment initiating position from which the tomographic image is started.

The distance measuring means may be any so long as it can measure the distance to the object. For example, the distance measuring means may comprise a measuring light source which emits distance measuring light toward the object, a photo-sensor which detects the reflected distance measuring light from the object when the distance measuring light is projected onto the object from the measuring light source, and a distance calculating means which calculates the distance to the object from the reflected distance measuring light detected by the photo-sensor.

The light source unit may emit a laser beam while sweeping the wavelength, while the image obtaining means obtains a tomographic image of the object by carrying out frequency-analysis such as Fourier-transform on the interference light, thereby detecting the intensity of the reflected light in the positions in the direction of depth of the object.

In accordance with the optical tomography system of the present invention, since the distance measuring means for measuring the distance from the probe to the object is provided so that the optical path length adjusting means adjusts the optical path length of the measuring light or the reference light by the use of the distance to the object measured by the distance measuring means to adjust the tomographic image obtainment initiating position from which the tomographic image is started, and the distance to the object is measured when the measurement initiating position upon obtainment of the tomographic image not by the interference light as when the tomographic image is obtained but by the distance measuring means, the signal processing on the interference light for detecting the measurement initiating position becomes unnecessary and the adjustment of the optical path length in the case where there is an individual difference between the probes and the adjustment of the optical path length so that the object is included in the measurable range of the tomographic image can be done in a short time.

Further, when the distance measuring means comprises a measuring light source which emits distance measuring light toward the object, a photo-sensor which detects the reflected distance measuring light from the object when the distance measuring light is projected onto the object from the measuring light source, and a distance calculating means which calculates the distance to the object from the reflected distance measuring light detected by the photo-sensor, the distance to the object can be accurately measured at high speed.

Especially, when the light source unit emits a laser beam while sweeping the wavelength, while the image obtaining means obtains a tomographic image of the object by carrying out frequency-analysis on the interference light, thereby detecting the intensity of the reflected light in the positions in the direction of depth of the object and obtaining a tomographic image of the object, the frequency analysis on the interference light for detecting the measurement initiating position becomes unnecessary and the adjustment of the optical path length so that the object is included in the measurable range of the tomographic image can be done in a short time.

Further, when the light source unit emits low coherence light, while the image obtaining means obtains a tomographic image of the object to detect the intensity of the reflected light in the positions in the direction of depth of the object by carrying out frequency-analysis on the interference light, the frequency analysis on the interference light for detecting the measurement initiating position becomes unnecessary and the adjustment of the optical path length so that the object is included in the measurable range of the tomographic image can be done in a short time.

DESCRIPTION OF THE PREFERRED EMBODIMENTS

Figure 1:
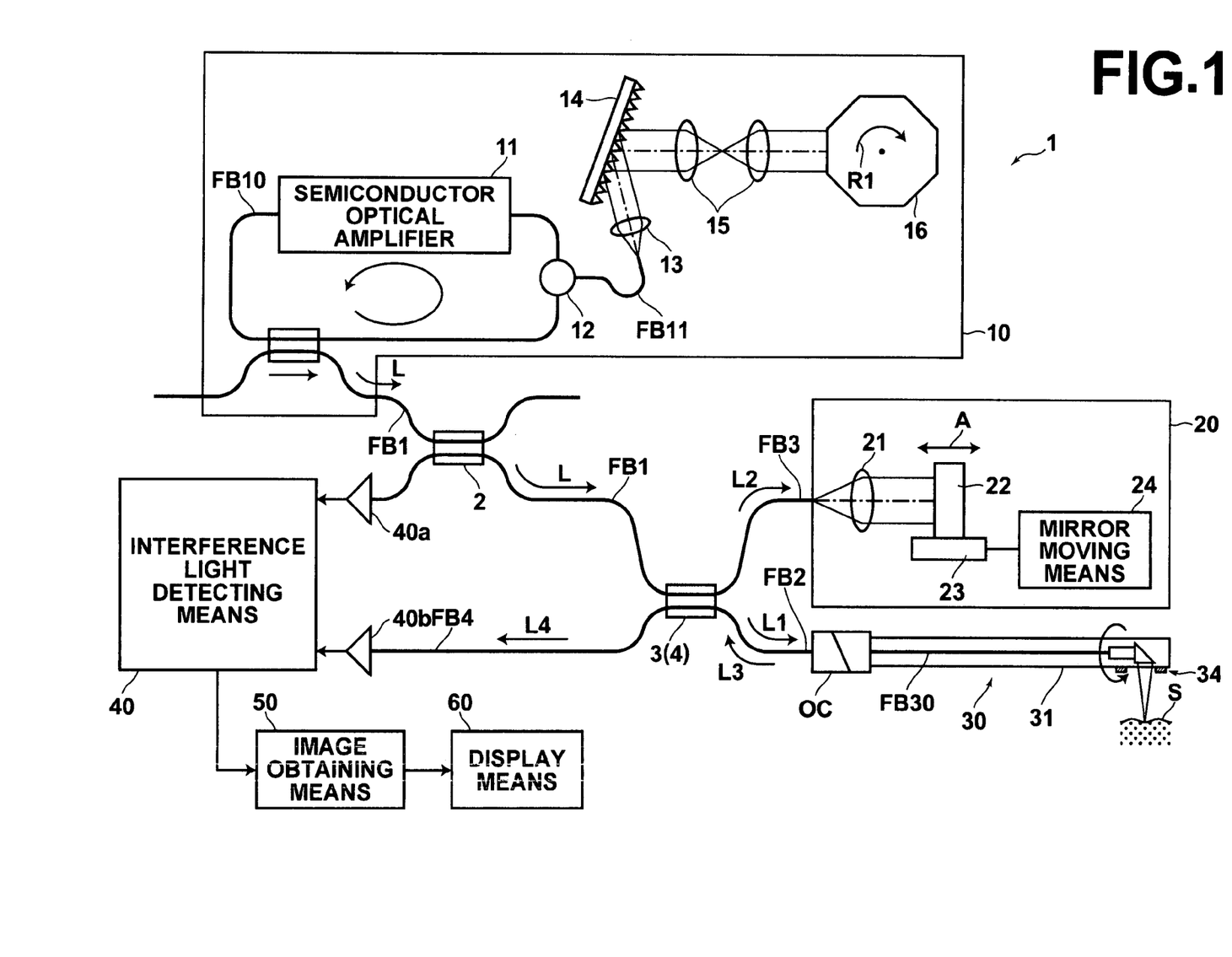
FIG. 1 is a schematic diagram showing an optical tomography system in accordance with a preferred embodiment of the present invention.

Embodiments of the present invention will be described in detail with reference to the drawings, hereinbelow. FIG. 1 is a schematic diagram that illustrates an optical tomography system in accordance with a preferred embodiment of the present invention. The optical tomography system 1 of this embodiment is for obtaining a tomographic image of an object of measurement such as a living tissue or a cell in a body cavity by measuring the SS-OCT. The optical tomography apparatus 1 of this embodiment comprises: a light source unit 10 for emitting a light beam L; a light dividing means 3 for dividing the light beam L emitted from the light source unit 10 into a measuring light beam L1 and a reference light beam L2; an optical path length adjusting means 20 for adjusting the optical path length of the reference light beam L2 divided by the light dividing means 3; a probe 30 which guides to the object S to be measured the measuring light beam L1 divided by the light dividing means 3; a multiplexing means 4 for multiplexing a reflected light beam L3 from the object S when the measuring light beam L1 is irradiated onto the object S, and the reference light beam L2; and an interference light detecting means 40 for detecting interference light beam L4 of the reflected light beam L3 and the reference light beam L2 which have been multiplexed.

The light source unit 10 emits the laser light beam L while sweeping the frequency at a constant period and comprises, for instance, a synchronized semiconductor laser. Specifically, the light source unit 10 comprises: a semiconductor optical amplifier 11 (semiconductor gain medium); and an optical fiber FB10 and the optical fiber FB10 is connected to both ends of the semiconductor optical amplifier 11. The semiconductor optical amplifier 11 functions to emit weak release light into a first end of the optical fiber FB10, when a drive current is injected there into, and to amplify the light that enters it from a second end of the optical fiber FB10. When the drive current is supplied to the semiconductor optical amplifier 11, a pulse-like laser light beam L is emitted to an optical fiber FB1 from a loop formed by the semiconductor optical amplifier 11 and the optical fiber FB10.

Further, an optical divider 12 is linked to the optical fiber FB10, and a portion of the light beam that propagates within the optical fiber FB10 is emitted into an optical fiber FB11 from the optical divider 12. The Light beam, which is emitted from the optical fiber FB11, passes through a collimating lens 13, a diffraction grating 14, and an optical system 15, to be reflected by a rotating polygon mirror 16. The light beam reflected by the rotating polygon mirror 16 reenters the optical fiber FB11.

The rotating polygon mirror 16 rotates in the direction indicated by arrow R1, to vary the angle of each reflective surface thereof with respect to the optical axis of the optical system 15. Thereby, only a light beam having a specific frequency, from among the light spectrally split by the diffraction grating 14, is returned to the optical fiber FB11.

Figure 2:
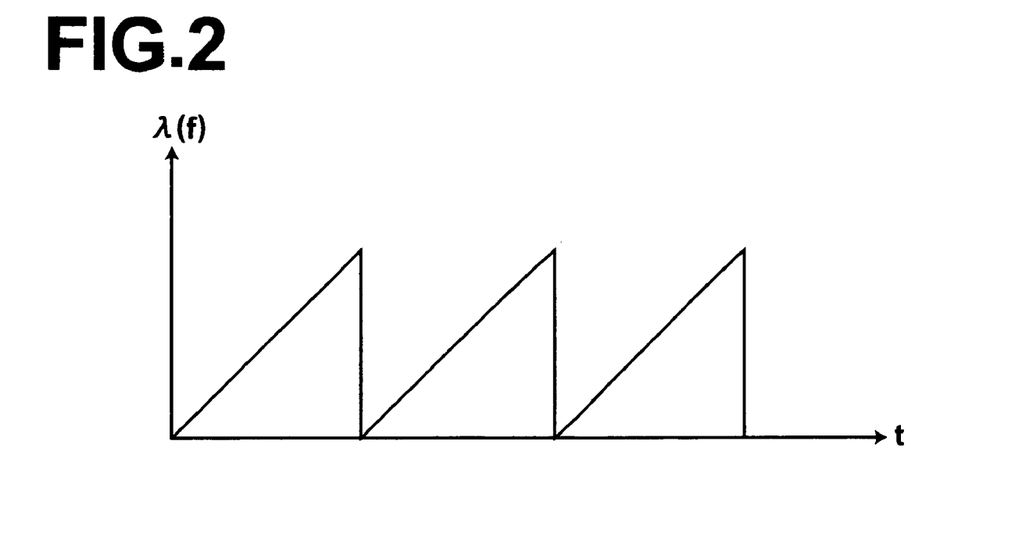
FIGS. 2 is a view for illustrating a state where the laser beam output from the light source unit shown in FIG. 1 fluctuates in its frequency.

The frequency of the light beam that reenters the optical fiber FB11 is determined by the angle formed by the optical axis of the optical system 15 and the reflective surface of the rotating polygon mirror 16. Accordingly, when the rotating polygon mirror 16 rotates in the direction indicated by arrow R1 at a constant speed, the wavelength of the light beam which reenters the optical fiber FB11 is swept at a period as shown in FIG. 2. As a result, a laser beam L which is swept in its wavelength at a period is emitted from the light source unit 10 toward the optical fiber FB1.

The light dividing means 3 comprises, for instance, a 2×2 fiber optic coupler and divides the light beam L led thereto by way of the optical fiber FB1 from the light source unit 10 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. In FIG. 1, the light dividing means 3 also functions as the multiplexing means 4. Alternately, the light dividing means 3 may be separate from the multiplexing means 4.

The probe 30 is optically connected to the optical fiber FB2 and the measuring light beam L1 is guided to the probe 30 from the optical fiber FB2. The probe 30 is inserted into a body cavity, for instance, through a forceps port by way of a forceps channel and is removably mounted on the optical fiber FB2 by an optical connector OC.

The optical path length adjusting means 20 is disposed on the side of the optical fiber FB3 radiating the reference light beam L2. The optical path length adjusting means 20 changes the optical path length of the reference light beam L2 in order to adjust the measurement initiation position with respect to the object S and comprises an optical system 21 and a reflecting mirror 22. The optical system 21 makes parallel the reference light beam L2 radiated from the optical fiber FB3 and at the same time, collects the reference light beam L2 reflected by the reflecting mirror 22 on the optical fiber FB3. The reflecting mirror 22 is disposed on a movable stage 23 which is moved in the direction of arrow A by a mirror moving means 24. In response to movement of the movable stage 23 in the direction of arrow A, the optical path length of the reference light L2 is changed.

The multiplexing means (or light combining means) 4 comprises a 2×2 fiber optic coupler, and multiplexes the reference light beam L2 which has been changed in its optical path length and its frequency by the optical path length adjusting means 20 and the reflected from the object S to emit the multiplexed light beam toward an interference light detecting means 40 by way of an optical fiber FB4.

The interference light detecting means 40 detects interference light L4 of the reflected lightbeam L3 and the reference light beam L2 which have been multiplexed by the multiplexing means 4. The image obtaining means 50 obtains a tomographic image of the object S by detecting the intensities of the reflected light beam L3 in positions in the direction of depth of the object S by carrying out frequency analysis on the interference light beam L4 detected by the interference light detecting means 40. In the embodiment shown in FIG. 1, an optical detector 40a which detects the intensity of the laser light beam L branched from an fiber optic coupler 2 of the optical fiber FB1 and an optical detector 40b which detects the intensity of interference light beam L4 are provided and the interference light detecting means 40 has a function of adjusting the balance of the intensity of the interference light beam L4 on the basis of the output of the optical detector 40a. This function suppresses unevenness in the light intensity by the frequency and permits to obtain a clearer image.

Here, detection of the interference light beam L4 in the interference light detecting means 40 and image generation in the image obtaining means 50 will be described briefly. Note that a detailed description of these two points can be found in M. Takeda, "Optical Frequency Scanning Interference Microscopes", Optical Engineering Contact, Vol. 41, No. 7, pp. 426-432, 2003.

When it is assumed that the light intensity of the interference fringes corresponding to each optical path length l when the reflected light beams L3 from depths of the object S and the reference light beam L2 interfere with each other with various optical path length differences is S(l), the light intensity I(k) detected in the interference light detecting means 40 is expressed by the following formula.

$$I(k)=\int_0^\infty S(l)[1+\cos(kl)]dl \quad (1)$$

wherein k represents the wave number and l represents the optical path length difference. Formula (1) may be considered to be given as an interferogram of a frequency range having a wave number of ω/c (k=ω/c). Accordingly, a tomographic image is obtained by obtaining information on the distance of the object S from the measurement initiating position and information on the intensity of reflection by carrying out frequency analysis by Fourier-transform on the spectral interference fringes detected by the interference light detecting means 40 and determining the intensity S(l) of the interference light L4.

Operation of the optical tomography system 1 having a structure described above will be described with reference to FIGS. 1 to 3, hereinbelow. When a tomographic image is to be obtained, the optical path length is first adjusted by moving the movable stage 23 in the direction of the arrow A so that the object S is positioned in the measurable area. The light beam L is subsequently emitted from the light source unit 10 by sweeping the wavelength at a period and the light beam L is divided into the measuring light beam L1 and the reference light beam L2 by the dividing means 3. The measuring light beam L1 is led by the optical probe 30 into a body cavity and is projected onto the object S. Then the reflected light beam L3 from the object S and the reference light beam L2 reflected by the reflecting mirror 22 are multiplexed, and the interference light beam L4 of the reflected light beam L3 and the reference light beam L2 is detected by the interference light detecting means 40. A tomographic image is obtained by carrying out frequency analysis on a signal of the detected interference light beam L4 in the image obtaining means 50.

The measurable area in the direction of depth where a tomographic image can be obtained by measurement of SS- OCT depends upon the frequency intervals of the measuring light L1 at which the measuring light L1 are measured (the number of the measuring points) and is limited. On the other hand, when the probe 30 is changed which is used for obtaining a tomographic image of the object S in a body cavity, it is necessary to adjust the optical path length in order to compensate for the error in length of the optical fiber of the probe 30. Further, when the object S is away from the probe 30, it is necessary to adjust the measurement initiating position to position the object in the measurable range. Accordingly, adjustment of the optical path length of the reference light according to the distance between the probe 30 and the object S becomes necessary. When the measurement initiating position is adjusted, there is a problem that when the position of the reflecting mirror 22 is adjusted after detection and Fourier-analysis of the interference light L4 are effected, the distance between the probe 30 and the object S cannot be known until the end of the Fourier-analysis, which takes a long time to adjust the measurement initiating position.

Figure 3:
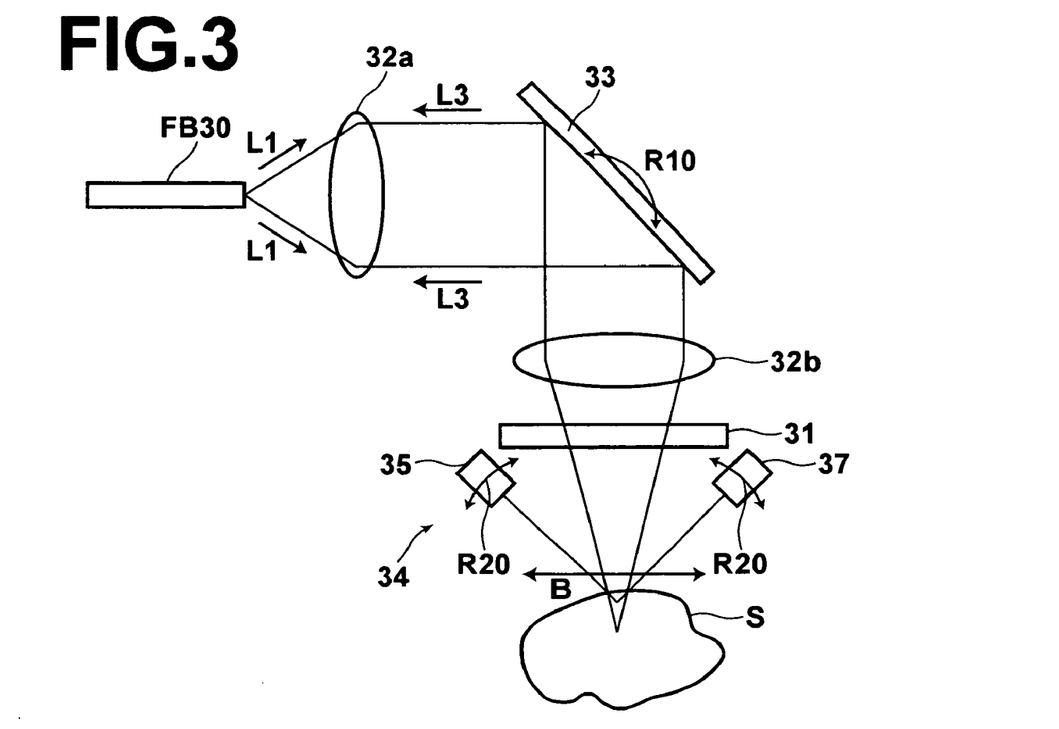
FIG. 3 is a schematic diagram of the probe of the optical tomography system shown in FIG. 1.

In the optical tomography system 1, the probe 30 is provided with a distance measuring means 34 for measuring the distance to the object S. FIG. 3 is a schematic view of an example of the leading end portion of the probe 30, and the probe 30 will be described with reference to FIG. 3, hereinbelow. The probe 30 comprises an optical fiber FB30 which guides the measuring light L1 and the reflected light L3, a tube 31 which covers the optical fiber, and a scanning mirror 33 which scans the measuring light L1 propagated through the optical fiber FB30 with respect to the object S and emits it toward the object S. The tube 31 is formed by a flexible and light-transmitting material such as, for instance, a resin and a cap for sealing the tube 31 is fixed to the leading end of the tube 31.

The measuring light L1 emitted from the optical fiber FB30 is collimated by a lens 32a, and is projected onto the object S by a lens 32b through the scanning mirror 33. The reflected light L3 which is reflected by the object S when the measuring light L1 is projected onto the object S is led to the optical fiber FB30 by way of the scanning mirror 33. The scanning mirror 33 changes the direction of the measuring light L1 by changing its angle in the direction of arrow R10 to cause the measuring light L1 to scan the object S in the direction of arrow B. With this arrangement, optical tomographic image of the object S in a body cavity can be obtained.

Figure 4:
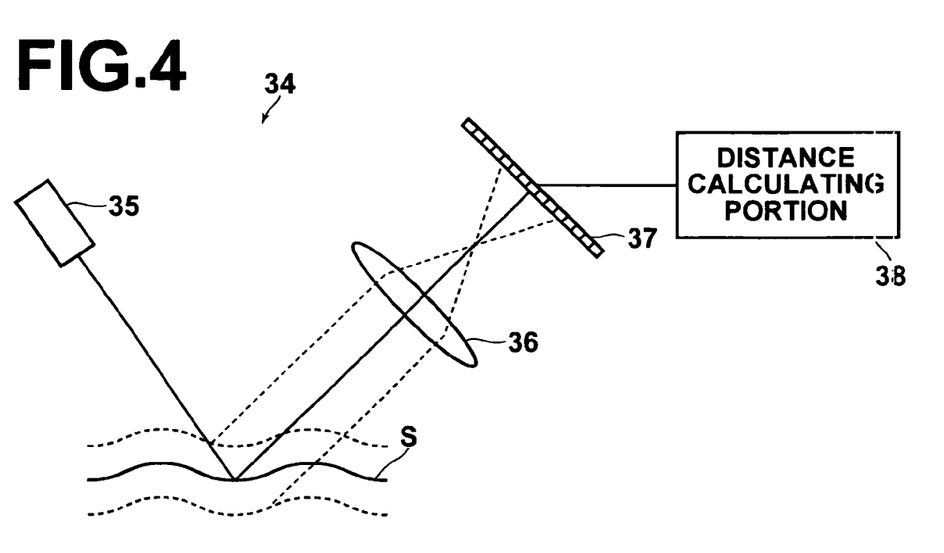
FIGS. 4 is a view for illustrating an example of the distance measuring means in the optical tomography system shown in FIG. 1.

The distance measuring means 34 is fixed to the inner surface, the outer surface or the inside of the tube 31. The distance measuring means 34 comprises, as shown in FIG. 4, a measuring light source 35 which emits distance measuring light, an imaging lens 36 which images the reflected distance measuring light which is reflected at the surface of the object S when the distance measuring light emitted from the measuring light source 35 is projected onto the surface of the object S, a photo-sensor 37 which detects the reflected distance measuring light imaged by the imaging lens 36, and a distance calculating means 38 which calculates the distance to the object S from the detected position of the reflected distance measuring light by the photo-sensor 37.

The measuring light source 35 inputs the distance measuring light comprising a collimated light beam obliquely with respect to the object S and the reflected distance measuring light which is reflected at the object S is input into the imaging lens 36. The photo-sensor 37 detects the reflected distance measuring light imaged by the imaging lens 36 by the use of a one-dimensional or two-dimensional array sensor. At this time, the reflected distance measuring light is imaged on the photo-sensor 37 by the imaging lens 36 in positions different from each other according to the distance between the measuring light source 35 and the object S. The distance calculating means 38 measures the distance between the probe 30 and the object S by the use of trigonometry on the basis of the position of the measuring light source 35 and the detected position of the reflected distance measuring light by the photo-sensor 37. The mirror moving means 24 of the optical path length adjusting means 20 moves the reflecting mirror 22 in the direction of arrow A on the basis of the distance detected by the distance calculating means 38 (FIG. 1).

By thus effecting adjustment of the measurement initiating position on the basis of the result of measurement by the distance measuring means 34, the adjustment can be carried out in a shorter time than the conventional, where the adjustment is carried out on the basis of the result of frequency-analysis of the interference light L4. Further even if the distance between the probe 30 and the object S is larger than the measurable range, it is possible to measure the distance between the probe 30 and the object S. Accordingly, adjustment of the measurement initiating position or the position of the probe can be done more efficiently in a shorter time.

Further, since the measuring light source 35 and the photo-sensor 37 are rotatable in the direction of arrow R20 as shown in FIG. 3, the position where the distance is to be measured can be searched in response to movement of the projecting position of the measuring light L1 in the direction of arrow B following rotation of the scanning mirror 33.

Figure 5:
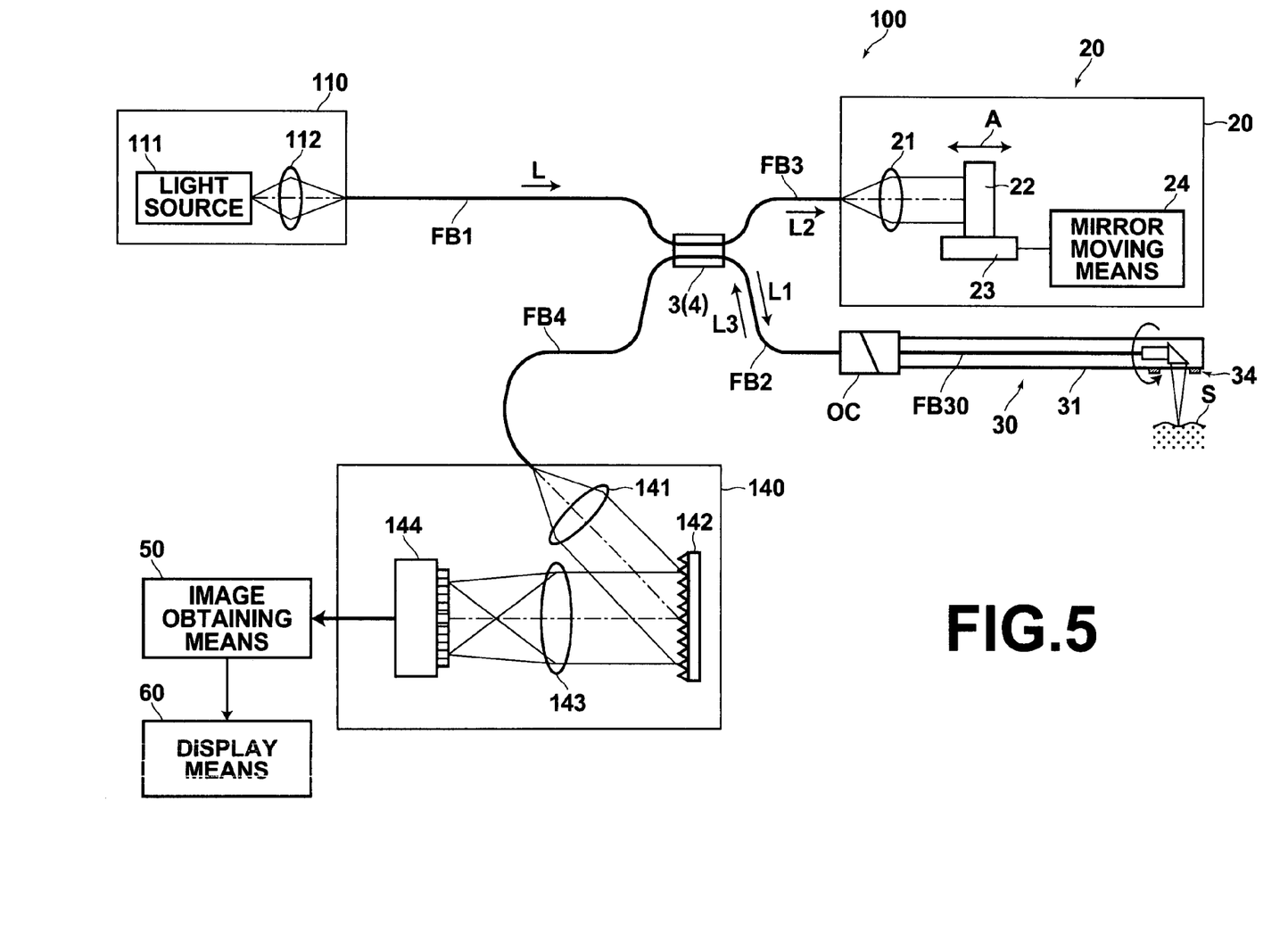
FIG. 5 is a schematic diagram showing an optical tomography system in accordance with a second embodiment of the present invention.

FIG. 5 is a schematic view showing an optical tomography system of the present invention in accordance with another embodiment. The optical tomography system 100 will be described with reference to FIG. 5, hereinbelow. In the optical tomography system 100 of FIG. 5, the parts analogous to those in the optical tomography system 1 of FIG. 1 are given the same reference numerals and will not be described here.

The optical tomography system 100 of FIG. 5 differs from the optical tomography system 1 of FIG. 1 in the arrangement of the light source unit and the interference light detecting means. Specifically, the optical tomography system 100 obtains a tomographic image by a so-called SD-OCT measurement and the light source unit 110 comprises a light source 111 which emits low coherence light such as SLD (super luminescent diode) or ASE (amplified spontaneous emission) and an optical system 112 for entering the light emitted from the light source 111 into the optical fiber FB1. Since the optical tomography system 100 of this embodiment is for obtaining a tomographic image with a living tissue in a body cavity taken as the object S, it is preferred that the light source 111 be, for instance, a broad spectral band, ultra short pulse laser where attenuation of light due to scatter and/or absorption when transmitted through the object S is minimized.

The interference light detecting means 140 detects interference light L4 of the reflected light beam L3 and the reference light beam L2 which have been multiplexed by the multiplexing means 4, and comprises a spectral means 142 which divides the interference light beam L4 having a plurality of wavelength bands by the wavelength bands and a light detecting means 144 which detects the amount of light of each wavelength band of the interference light beam L4 divided by the spectral means 142. The spectral means 142 comprises, for instance, a diffraction grating element, and divides the interference light beam L4 entering it from an optical fiber FB4 by way of the collimator lens 141 to output the divided interference light beam L4 to the light detecting means 144.

The light detecting means 144 is formed by a plurality of photo sensors which comprises a plurality of, for instance, one-dimensionally or two-dimensionally arranged CCDs and each of the photo sensors detects each wavelength band of the interference light beam L4 entering by way of an optical system 143. In the light detecting means 144, the interference light L4 where the spectrum of the light source unit 110 is added with a Fourier-transformed function of information on the reflection is observed. Then, by carrying out frequency analysis in the image obtaining means 50 on the interference light beam L4 detected in the interference light detecting means 140, reflection information in the position of depth can be obtained.

Also in FIG. 5, the optical path length adjusting means 20 has a function of adjusting the optical path length of the reference light L2 in order to adjust the measurement initiating position. By moving the reflecting mirror 22 in the direction of arrow A on the basis of the distance to the object S measured by the distance measuring means 34, the measurement initiating position is adjusted. With this arrangement, the adjustment can be effected in a shorter time than the conventional, where the adjustment has been done on the basis of the interference light L4.

Figure 6:
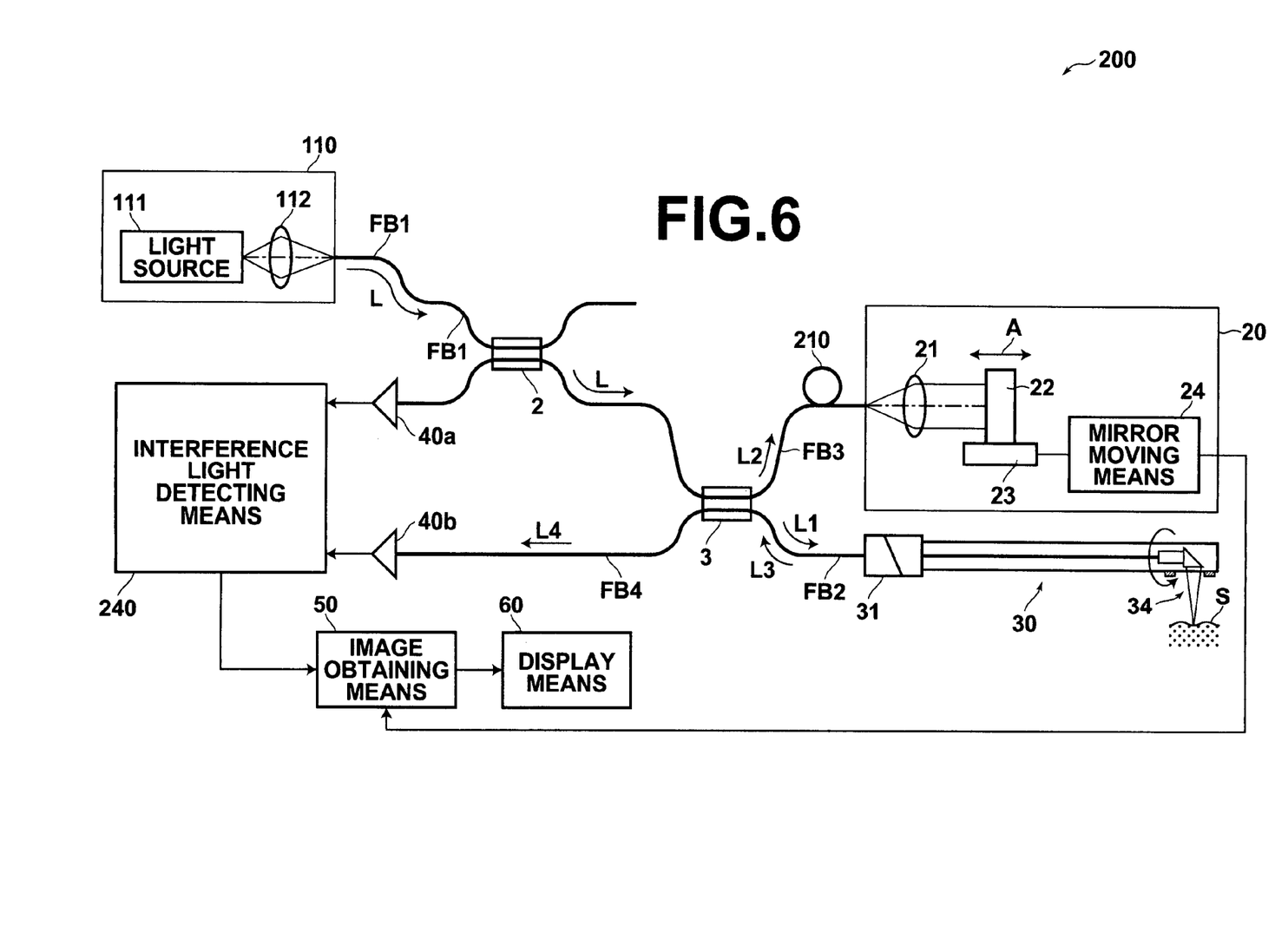
FIG. 6 is a schematic diagram showing an optical tomography system in accordance with a third embodiment of the present invention.

FIG. 6 is a schematic view showing an optical tomography system of the present invention in accordance with still another embodiment. The optical tomography system 200 will be described with reference to FIG. 6, hereinbelow. In the optical tomography system 200 of FIG. 6, the parts analogous to those in the optical tomography system 1 and 100 of FIGS. 1 and 5 are given the same reference numerals and will not be described here.

The optical tomography system 200 obtains a tomographic image by a so-called SD-OCT measurement and the optical path length adjusting means 20 has a function of changing the optical path length of the reference light L2 in order to change the measuring position in the object S. A phase modulator 210 is disposed on the optical path (optical fiber FB3) to give a slight frequency shift to the reference light L2. The reference light L2 which has been changed in its optical path length and shifted in its frequency by the optical path length adjusting means 20 is guided to the optical fiber FB4 or the multiplexing means 4.

Interference light detecting means 240 detects the intensity of the interference light L4 by, for instance, heterodyne detection. Specifically, when the sum of the total optical path length of the measuring light L1 and the total optical path length of the reflected light L3 is equal to the total optical path length of the reference light L2, a beat signal which varies in intensity at the difference frequency between the reference light L2 and the reflected light L3 is generated. As the optical path length is changed by the optical path length adjusting means 20, the measuring position (measuring depth) in the object S changes and the interference light detecting means 240 comes to detect beam signals in the measuring positions. On the basis of the beat signals detected by the interference light detecting means 240 and information on the measuring position in the mirror moving means 24, a tomographic image is generated.

Also in the optical tomographic system 200 where TD-OCT measurement is carried out, by providing the probe 30 with the distance measuring means 34, the adjustment of measurement initiating position can be more accurately effected in a shorter time than the conventional, where the search of the measurement initiating position has been done while the reflecting mirror is caused to scan.

In the embodiments described above, since the probe 30 is provided with the distance measuring means 34 and the optical path length of the reference light is adjusted by the use of the distance to the object S measured by the distance measuring means 34, when the tomographic image is obtained, the measurement initiating position is set on the basis of the distance to the object measured not by the use of the interference light as in obtaining the tomographic image but measured by the distance measuring means, whereby the signal processing on the interference light to detect the measurement initiating position becomes unnecessary and the adjustment of the optical path length so that the object is included in the measurable range can be done in a short time.

Further, when the distance measuring means 34 comprises a measuring light source 35 which emits distance measuring light toward the object S, a photo-sensor 37 which detects the reflected distance measuring light from the object S when the distance measuring light is projected onto the object S from the measuring light source 35, and a distance calculating means 38 which calculates the distance to the object S from the reflected distance measuring light detected by the photo-sensor 37 as shown in FIG. 3, the distance to the object S can be accurately measured at high speed.

The distance measuring means 34 described above may be applied to any one of the optical tomography systems 1 (FIG. 1: SS-OCT), 100 (FIG. 5: SD-OCT) and 200 (FIG. 6: TD-OCT).

The present invention is not limited to the above embodiments. For example, though the distance measuring means 34 shown in FIGS. 3 and 4 measures the distance by the use of trigonometry, by way of example, the distance may be measured in a short distance by any one of known technics such as by the ultrasonic waves, by the sharpness of a CCD image imaged by a lens or by an optical distance measuring method so long as the system can be compactly accommodated.

Further, though, in FIGS. 1, 5 and 6, the optical path length adjusting means 20 adjusts the optical path length of the reference light L2, by way of example, the optical path length adjusting means 20 may adjust the optical path length of the measuring light L1. In this case, for example, a three-way optical circulator is provided in the optical fiber FB2 which guides the measuring light L1 and the optical path length adjusting means 20 is interposed in a vacant port. The return light from the object S is led to the optical path length adjusting means 20, and the reflected light from the reflecting mirror 22 at the terminal end of the optical path length adjusting means 20 is returned to the multiplexing means 4.

What is claimed is;

1. An optical tomography system for obtaining a tomographic image of an object to be measured comprising
   a light source unit which emits light,
   a light dividing means which divides light emitted from the light source unit into measuring light and reference light,
   an optical path length adjusting means which adjusts an optical path length of the measuring light or the reference light which has been divided by the light dividing means,
   a probe which guides the measuring light to the object,
   a light combining means which combines the reflected light from the object when the measuring light is projected onto the object and the reference light,
   an interference light detecting means which detects interference light of the reflected light and the reference light which have been combined by the light combining means, and
   a tomographic image obtaining means which obtains a tomographic image of the object on the basis of the interference light detected by the interference light detecting means,
   the probe being provided with a distance measuring means for measuring the distance from the probe to the object, and the optical path length adjusting means adjusting the optical path length of the measuring light or the reference light by the use of the distance to the object measured by the distance measuring means to adjust the tomographic image obtainment initiating position from which the tomographic image is started.

2. An optical tomography system as defined in claim 1 in which the distance measuring means comprises a measuring light source which emits distance measuring light toward the object, a photo-sensor which detects the reflected distance measuring light from the object when the distance measuring light is projected onto the object from the measuring light source, and a distance calculating means which calculates the distance to the object from the reflected distance measuring light detected by the photo-sensor.

3. An optical tomography system as defined in claim 2 in which the photo sensor comprises a plurality of photo detectors arranged in a line, and the distance calculating means calculates distance based on which of the plurality of photo detectors detects the light reflected from the object.

4. An optical tomography system as defined in claim 3 in which the distance calculating means calculates the distance by the use of trigonometry.

5. An optical tomography system as defined in claim 2 in which the distance to the object is based on an exterior surface of a target, and wherein the reflected distance measuring light is reflected off of the exterior surface of the target.

6. An optical tomography system as defined in claim 1 in which the light source unit emits a laser beam while sweeping the wavelength, while the image obtaining means obtains a tomographic image of the object by carrying out frequency-analysis on the interference light, and the optical path length adjusting means changes the optical path length of the measuring light or the reference light to a position to obtain a tomographic image signal.

7. An optical tomography system as defined in claim 1 in which the light source unit emits low coherence light, while the image obtaining means obtains a tomographic image of the object by carrying out frequency-analysis on the interference light, and changes the optical path length of the measuring light or the reference light to a position to obtain a tomographic image signal.

8. An optical tomography system as defined in claim 1 in which the interference light detecting means comprises a spectral means which divides the interference light, and a light detecting means which detects the divided interference light.

9. An optical tomography system as defined in claim 8 in which the spectral means divides the interference light into wavelength bands.

* * * * *